(12) United States Patent
Schlein et al.

(10) Patent No.: US 7,393,694 B1
(45) Date of Patent: Jul. 1, 2008

(54) CHEMICAL AND BIOLOGICAL SAMPLING DEVICE AND KIT AND METHOD OF USE THEREOF

(75) Inventors: Mark S. Schlein, Abingdon, MD (US); Peter A. Emanuel, Abingdon, MD (US); Kevin S. Wallace, Elkton, MD (US); Peter J. Schlitzkus, Baltimore, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 461 days.

(21) Appl. No.: 11/264,337

(22) Filed: Oct. 26, 2005

Related U.S. Application Data (62) Division of application No. 09/974,436, filed on Oct. 10, 2001, now Pat. No. 7,022,289.

(51) Int. Cl.
*G01N 1/00* (2006.01)

(52) U.S. Cl. .................. 436/176; 436/174; 436/177; 436/178; 422/58; 422/68.1; 422/102

(58) Field of Classification Search .............. 422/58, 422/68.1, 99, 101, 102; 436/177, 178; 220/213, 220/288, 303, 601, 669, 745, 796; 600/562, 600/569, 570, 572, 573
See application file for complete search history.

(56) References Cited

U.S. PATENT DOCUMENTS

| | | | | |
|---|---|---|---|---|
| 3,449,081 A * | 6/1969 | Hughes | .................. | 422/61 |
| 3,513,830 A * | 5/1970 | Kalayjian | ................. | 600/572 |
| 3,792,699 A * | 2/1974 | Tobin et al. | .................. | 600/572 |
| 3,890,954 A * | 6/1975 | Greenspan | .................. | 600/572 |
| 3,906,933 A * | 9/1975 | Tur et al. | ..................... | 600/572 |
| 3,954,564 A * | 5/1976 | Mennen | ........................ | 600/572 |
| 4,018,653 A * | 4/1977 | Mennen | ....................... | 600/572 |
| 4,150,950 A * | 4/1979 | Takeguchi et al. | ......... | 435/252.1 |
| 4,223,093 A * | 9/1980 | Newman et al. | .............. | 600/572 |
| 4,353,868 A * | 10/1982 | Joslin et al. | .................. | 422/101 |
| 4,409,988 A * | 10/1983 | Greenspan | ................... | 600/572 |
| 4,707,450 A * | 11/1987 | Nason | ........................... | 600/572 |
| 4,813,432 A * | 3/1989 | Saint-Amand | ............... | 600/562 |
| 4,848,167 A | 7/1989 | Gordon et al. | ............ | 73/864.71 |
| 5,078,968 A * | 1/1992 | Nason | ........................... | 422/58 |
| 5,091,316 A * | 2/1992 | Monthony et al. | ........... | 600/572 |
| 5,124,041 A * | 6/1992 | Sheer et al. | ................... | 210/641 |
| 5,129,402 A * | 7/1992 | Koll et al. | ..................... | 600/572 |
| 5,726,062 A * | 3/1998 | Numa et al. | ................... | 436/86 |

(Continued)

*Primary Examiner*—Jill Warden
*Assistant Examiner*—Dwayne K Handy
(74) *Attorney, Agent, or Firm*—Ulysses John Biffoni (57) ABSTRACT

A self-contained, leak-proof sampling device and kit employing said device for collecting chemical and biological samples from various surfaces. The invention provides a sampling device and kit that may be employed to easily collect chemical and biological samples, safely transport the collected samples, safely dispense collected samples for analysis and provide optimum sample recovery. The sampling device is in the form of a leak proof container that comprises a lid and base. The lid contains a sterile absorbent collection means integrated into and positioned on the inside surface of the lid. The base contains a means to facilitate sample recovery from the absorbent collection means via compression and/or scraping of the absorbent collections means. Methods for employing the present invention are described herein.

13 Claims, 5 Drawing Sheets

U.S. PATENT DOCUMENTS

| | | | |
|---|---|---|---|
| 5,827,675 A * | 10/1998 | Skiffington et al. | 435/8 |
| 5,830,154 A | 11/1998 | Goldstein et al. | 600/572 |
| 5,846,209 A * | 12/1998 | Hakalehto | 600/572 |
| 6,021,681 A * | 2/2000 | Jezek | 73/864.71 |
| 6,176,836 B1 | 1/2001 | Trudil et al. | 600/572 |
| 6,328,931 B1 * | 12/2001 | Silver et al. | 422/52 |
| 6,524,530 B1 * | 2/2003 | Igarashi et al. | 422/58 |
| 6,548,018 B2 * | 4/2003 | DiCesare et al. | 422/52 |
| 7,022,289 B1 * | 4/2006 | Schlein et al. | 422/102 |

* cited by examiner

CHEMICAL AND BIOLOGICAL SAMPLING DEVICE AND KIT AND METHOD OF USE THEREOF

This application is a division of application Ser. No. 09/974,436 filed Oct. 10, 2001, now U.S. Pat. No. 7,022,289.

GOVERNMENT INTEREST

The invention described herein may be manufactured, used and licensed by or for the U.S. Government.

BACKGROUND OF THE INVENTION (1) Field of the Invention

The present invention relates to a sampling device and kit for collecting chemical and biological samples in a wet or dry format. The invention provides a means to easily collect chemical and biological samples, safely transport the collected samples with no leakage, and safely dispense a collected sample into a sterile capture vial/bottle for analysis. The present invention provides for optimum sample recovery and has been designed to be easy to operate while wearing protective gear.

(2) Description of Related Art

Numerous devices and kits are available for collecting samples of chemical and biological matter to be analyzed for their content.

Presently, the Joint Program Office for Biodefense fields a cotton swab based sampling kit for use with hand-held assays. These sampling kits and hand-held assays are only available to Government agencies. This cotton swab based sampling kit is a single use kit that only permits the sampling of small areas. It is used with hand held assays wherein the collected sample is tested as collected. The kit does not provide a means in which to safely transport a collected sample for subsequent confirmation analysis or further testing. Although this single use kit is a cost effective means to sample suspected laboratories and production plants, it was not intended to be used to sample larger areas, such as construction sites and subways.

EAI Corporation, under arrangements with New Horizons Diagnostics, markets a biological sampling kit as BIO-HAZ® kit. This biological sampling kit is a swipe-type kit that employs the use of a sponge and is used in field bio-sampling missions. While this kit is effective in collecting biological samples, it contains many parts and bags, which makes its use cumbersome and difficult to use in hostile environments. Use of this kit requires the tearing of bags, handling of vials, and manipulation of tiny pieces all of which are time consuming and difficult to accomplish especially while wearing protective hazmat suits.

Trudil et al., U.S. Pat. No. 6,176,836 describes a biological sample collection kit that employs numerous parts that require careful handling during sample collection. The kit requires the operator to tear open sterile bags so as to be able to employ the sterile parts therein—i.e., sponge, swab, pipette, etc.

Another biological sampling device, which was manufactured by Truetech and described in U.S. Pat. No. 4,848,167 to Gordon et al., is a portable sampling unit that employs a dry Velcro® sampling pad. Once a sample has been collected using the dry sampling pad, the sample-containing pad is washed with a buffer by cracking a buffer filled ampule. The ampule is cracked by pinching the unit. The buffer washes over the pad and the sampling unit is vigorously shaken. The collected sample is then dispensed by extending the sample port to allow drops of fluids to be released from the sampling port. This sampling unit delivers only sufficient buffer for three test tickets. The sampling device does not provide a means to archive and/or transport a sample for future analysis.

An additional chemical and biological sampling unit is available in the form of a sampling backpack, which is marketed by Quicksilver, Inc. This unit comprises tweezers, scalpels, swabs, and various other instruments for collecting samples of various shapes, sizes and/or forms. This kit, like some of those described above, contains numerous parts that may require careful, intricate handling by an operator.

There remains a need to provide a biological and chemical sampling device/kit that provides an easier more efficient means for collecting samples from large surface areas, storing said samples, transporting the same, and dispensing them for testing. The present invention does not require the use of numerous instruments, vials and bags, or the testing of the sample as collected.

The present invention provides for a self-contained chemical and biological sample collection device and kit employing said device which can be used to (1) easily and safely sample large surface areas; (2) safely store collected samples to be transported for later analysis; and (3) safely dispense collected samples for testing. Moreover, the present invention has been designed to be simple to operate even while wearing protective gear.

SUMMARY OF THE INVENTION

The present invention provides a self-contained sampling device and kit employing said device for collecting chemical and biological samples. The invention provides a sampling device and kit that may be employed to easily collect chemical and biological samples, safely transport the collected samples with no leakage, safely dispense a collected sample for analysis and provide optimum sample recovery. Methods for employing the present invention are described herein.

The present invention provides a portable and disposable, self-contained, leak proof, sampling device that may be used to collect samples from various surfaces such as laboratory benches, combat theatre surfaces, food manufacturing plant surfaces, etc. Surfaces from which samples may be collected include, but are not limited to, concrete, vinyl, wood, glass, and nylon. Collection of the samples may be accomplished under wet or dry conditions. The sampling device is essentially in the form of a leak proof container having a lid and base each of which have specific properties so as to facilitate the safe and efficient sampling of various surfaces and provide for a means to transport a collected sample without contamination of the collected sample within the device or the environment surrounding the sampling device when in the closed position. The lid and base of the self-contained sampling device within the scope of the present invention may be closed/sealed in any fashion so as to isolate the contents therein so as to prevent contamination of the collected sample or of the exterior surroundings during transport. It is critical that the sampling device be leak-proof. To achieve this, for example, the lid may tightly screw onto the base.

The lid of the self-contained sampling device herein contains a sterile absorbent collection means, such as a sponge, which is integrated into and positioned on the inside surface of the lid so that when the self-contained sampling device is in the closed position, the sterile absorbent collection means is present inside the sampling device. The sterile absorbent collection means is positioned in the lid in a fashion so as to facilitate the collection of a sample, wherein sample collection is accomplished by merely swiping the lid containing the sponge, for instance, therein sponge-side down along a test surface. In the present invention, the sterile absorbent collection means extends a sufficient amount from the lid so that during sample collection, the absorbent collection means comes into direct contact with the surface from which a sample is sought. Once a sample is collected on the sponge, for instance, the lid is replaced on the base in a fashion so that the sample is confined to the container without leakage.

The base of the sampling device contains a means to facilitate sample recovery from the absorbent collection means via compression and/or scraping of the absorbent collection means. The means to facilitate sample recovery from the absorbent collection means may be in the form of grooves or ridges molded into or positioned in the base or a screen positioned within said base in such a way that when the container is being closed and is in its closed position the grooves or ridges, for instance, squeeze and compress, as well as scrape, the absorbent collection means thereby releasing the collected sample from the absorbent collection means and into the base itself.

Sample collection is accomplished by removing the lid from the sampling device and swiping the sterile absorbent collection means integrated therein along a surface from which a sample is desired. Sample collection may be accomplished using the sterile absorbent collection means in a wet or dry state. If a wet, sterile absorbent collection means is employed, a buffer is used to wet the absorbent collection means prior to sample collection. The buffer may be provided in the self-contained sampling device itself or may be added to the sampling device or absorbent collection means just prior to deployment or sampling so as to pre-wet the absorbent collection means prior to sample collection. The lid of the sampling device may, for example, screw onto the base to seal the buffer and wetted absorbent collection means until needed for sample collection. Collection of a sample may also be accomplished using a dry absorbent collection means in which case no buffer is added to the sampling device or absorbent collection means prior to sample collection. As an alternative to the above, buffer may be poured directly onto the surface from which a sample is desired and the absorbent collection means then swiped across the surface.

In any case, once the test surface is swiped with the absorbent collection means as described above, the lid containing the absorbent collection means and the sample thereon is returned to the base and securely positioned/fastened thereon. The collected sample may then be safely transported in the leak-proof sampling device for testing, evaluation and archiving.

If a dry absorbent collection means is used in the collection of a sample, the dry absorbent collection means containing the sample may be later hydrated with a buffer so as to facilitate retrieval of the collected sample using the compression/scraping action described above. Delivery of the liquid sample to a sterile receptacle, i.e., a dropper bottle, for testing and archiving may be accomplished using conventional laboratory techniques, such as, using an eye-dropper or pipette.

The base of the sampling device may optionally be designed so as to (1) contain a tool to facilitate the transfer of a collected sample from it to a separate receptacle, such as a sterile vial, or (2) provide a means to have a sterile, sample capture vial removably attached to its lower outer surface so that the collected sample would flow directly into the capture vial. The tool to facilitate the transfer of a collected sample may be in the form, for example, of a spigot or spout or a screw-on dropper attachment. The preferred embodiment of the invention employs a sterile capture vial that is removably attached to the base. The presence of this feature avoids the step of having to transfer or dispense a collected sample from the base into a separate sterile receptacle for analysis. Moreover, if the preferred embodiment is used, the capture vial containing a collected sample could be detached from the sampling device once sampling is completed, then sealed and transported.

It is an object of the present invention to provide a portable, self-contained chemical and biological sampling device and kit to easily and safely sample surface areas.

It is a further object of the present invention to provide a portable, self-contained chemical and biological sampling device that may be used to safely collect, store, transport and dispense collected samples for testing.

A further object of the invention is to provide a sampling device for collecting and delivering bacteria, virus, toxins and chemical agents in a liquid sample large enough for extensive testing and archiving.

Still a further object of the invention is to provide a self-contained chemical and biological sampling device and kit that can be easily employed to collect samples while wearing protective gear.

Yet a further object of the present invention is to provide a chemical and biological sampling kit employing a portable, self-contained chemical and biological sampling device, a vial containing a buffer substance, and a sterile receptacle with a dropper attachment.

A further object of the present invention is to provide a method to safely and simply collect, transport, store and dispense chemical and biological samples found on various surfaces.

The means to achieve these and other objectives of the present invention will be apparent from the following detailed description of the invention, drawings and claims.

BRIEF DESCRIPTION OF THE DRAWINGS

In the drawings:

FIG. 1 is a schematic drawing of an embodiment of a self-contained sampling device within the scope of the invention, wherein grooves are depicted as being molded into the base of the sampling device so as to facilitate sample recovery from the absorbent collection means (i.e., sponge).

FIG. 2 is a schematic drawing of another embodiment of a self-contained sampling device within the scope of the invention, wherein a screen is illustrated as the means for facilitating sample recovery from the absorbent collection means.

FIG. 3 is a schematic drawing of yet another embodiment of a self-contained sampling device within the scope of the invention, wherein the base contains a spout molded therein.

FIG. 4 is a schematic drawing of the preferred embodiment of a self-contained sampling device within the scope of the invention, wherein a sterile, sample capture bottle/vial is removably attached to the base of the sampling device so as to capture collected samples therein. In this embodiment, collected samples are deposited directly into the sample capture bottle.

FIG. 5 is a cut-away, schematic view of the preferred embodiment illustrated in FIG. 4.

DETAILED DESCRIPTION OF THE INVENTION

The present invention provides a self-contained sampling device and kit employing said device for collecting chemical and biological samples. The invention has been designed to be easy to operate when donning chemical and biological hazardous protective gear. It has also been designed so as to provide a means to safely transport a sample without having it leak. Use of the sampling device within the scope of the present invention minimizes and/or eliminates the potential for contamination of a collected sample. The invention is described herein with reference to the drawings.

Reference numeral 3 is used in the description of the invention to generically identify the sampling device within the scope of the present invention. The addition of a "prime," "double prime," "triple prime," etc. notation to the reference numeral 3 (i.e., 3', 3", 3''') is used in the figures to illustrate different embodiments of the invention. Other reference numerals are used consistently throughout the figures to identify the same features.

Figure 1:
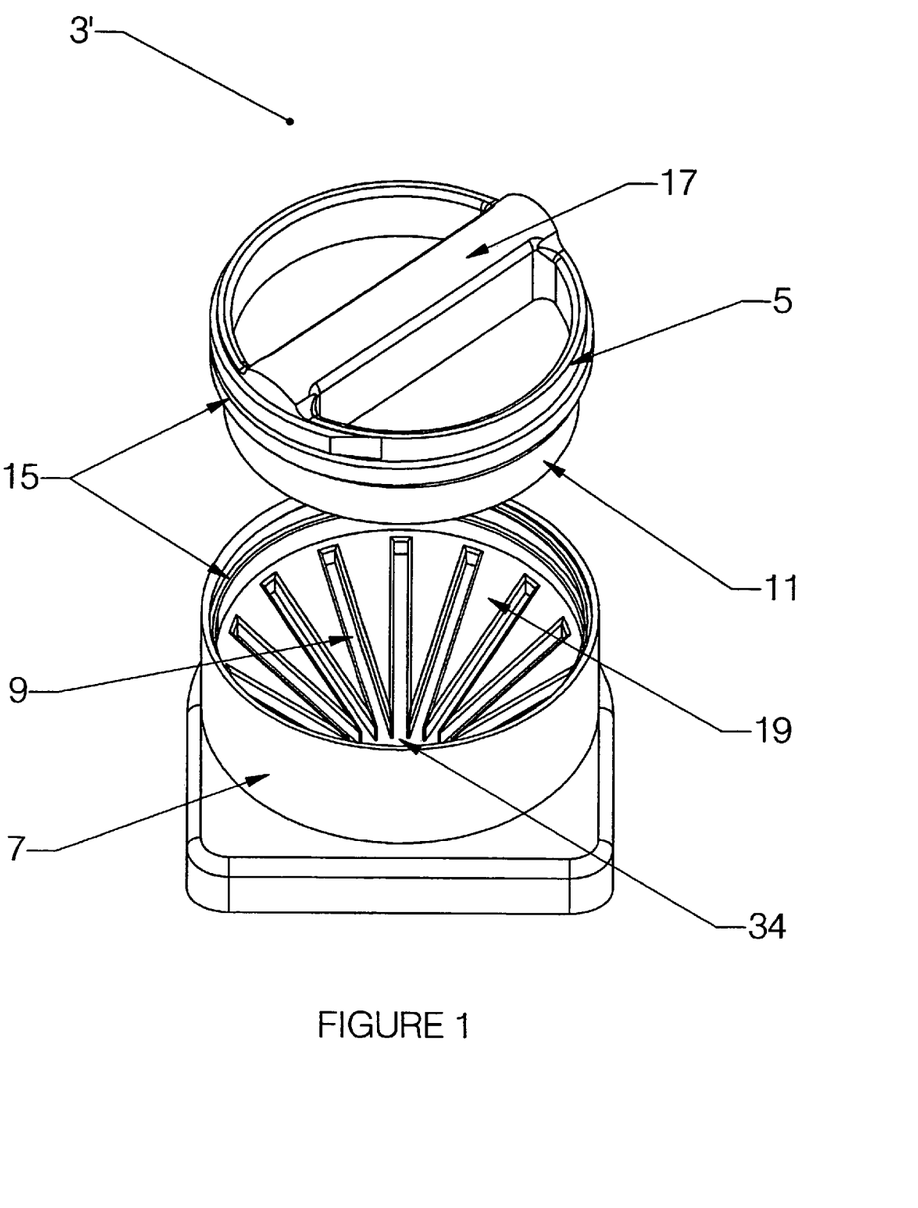

An embodiment of the sampling device 3 of the present invention is set forth in FIG. 1. The sampling device 3' therein generally comprises a lid 5 and a base 7. Lid 5 has integrated on its interior surface a sterile absorbent collection means 11, such as a sponge. The sponge 11 is positioned on the interior surface of the lid 5 in a fashion so as to facilitate the collection of a sample by an operator, wherein the operator may hold the lid 5, for example only using optional handle 17, and swipe the sponge 11 against a surface (not shown) from which a sample is desired. The sponge 11, or other sterile absorbent collection means, extends a sufficient amount from said lid 5 so as tQ come into contact with the surface from which a sample is desired. Base 7 contains a means to facilitate sample recovery 9 from the absorbent collection means 11 via compression and/or scraping. The means to facilitate sample recovery 9 is illustrated in FIG. 1 as grooves 9 which may be either molded into or positioned in the base 7. The grooves 9, or any other means to facilitate sample recovery, are positioned so as to come into contact with the absorbent collection means 11 and compress and/or scrape the absorbent collection means 11 when the self-contained sampling device 3 is being closed and in the closed position. Compression and/or scraping of the absorbent collection means 11 facilitates the release from the absorbent collection means 11 of a collected sample. The design and shape of the grooves 9 may vary so long as they are present and positioned in the base 7 in a fashion so as to facilitate sample recovery as described herein. The interior bottom surface 19 of the base 7 may be pitched at a particular angle/incline so as to facilitate flow of a collected sample into a particular area (i.e., reservoir 34) of the base 7 so as to help optimize sample recovery.

The sampling device 3' may be closed (not illustrated) by positioning the lid 5 over the base 7 in a conventional fashion so as to create a seal there-between so as to prevent the flow/release of any contents therein to the surrounding environment and to prevent the contamination of the contents therein. For example, lid 5 may be screwed on to base 7 via threads 15. Any conventional means, however, for creating a seal between the lid 5 and base 7 may be employed herein. One having ordinary skill in the art will be able to select the appropriate means within which to design the interface between the lid 5 and the base 7 so as to prevent any cross contamination between the contents of the sampling device 3' and the environment surrounding it.

Figure 2:
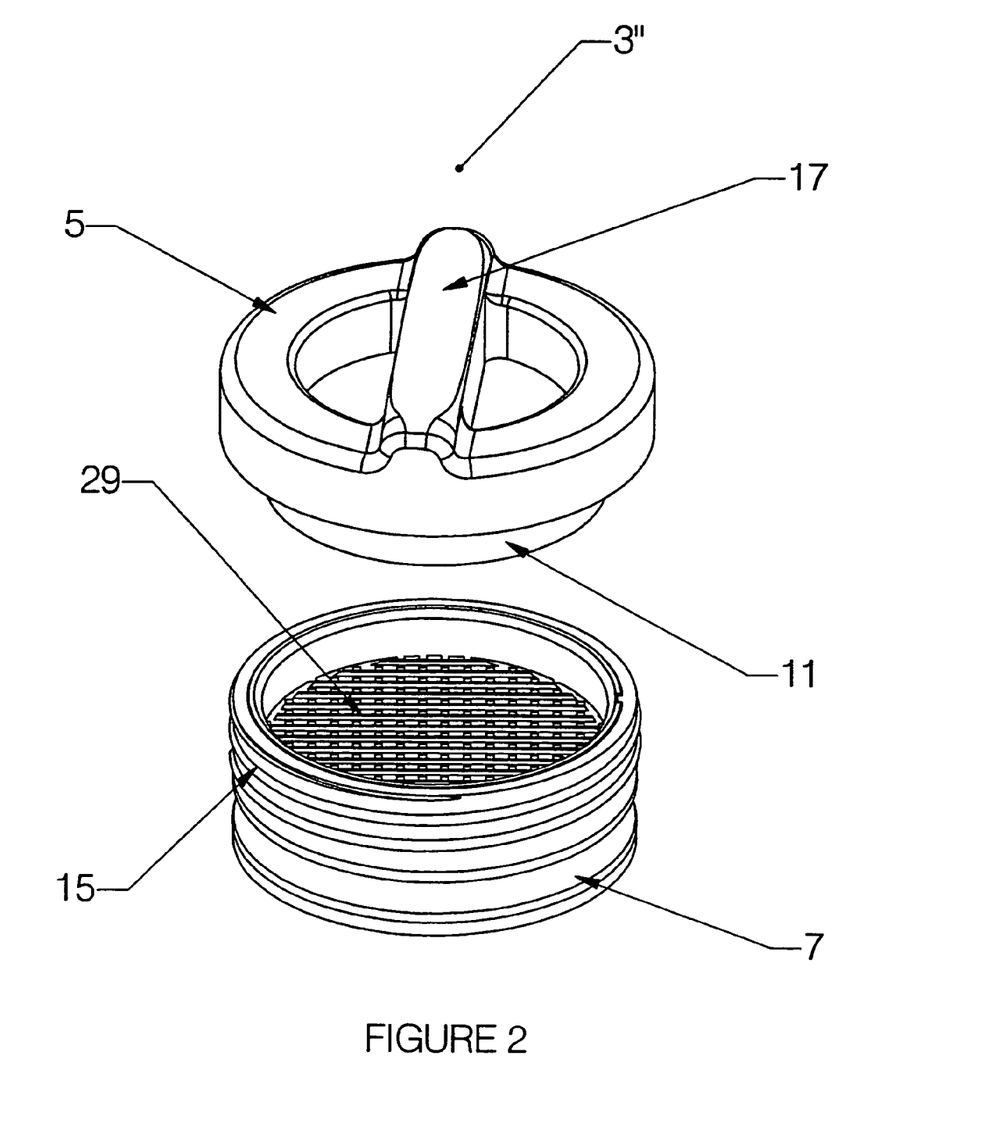

FIG. 2 illustrates an additional embodiment of the sampling device 3 of the present invention. This embodiment, illustrated as sampling device 3", employs a screen 29 as the means for facilitating sample recovery from the absorbent collection means 11. Screen 29 is positioned in the base 7 so as to compress and/or scrape the absorbent collection means 11 when the sampling device 3" is being closed or is in the closed position.

Figure 3:
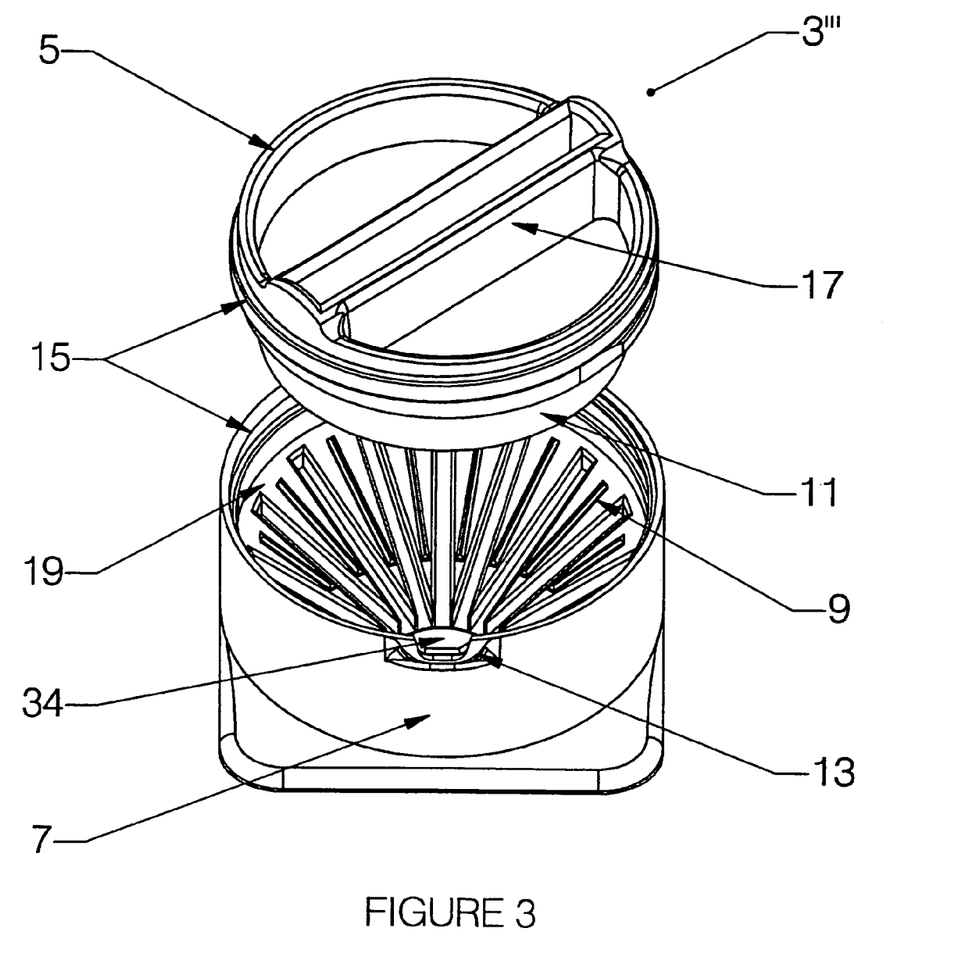

Another embodiment of the present invention is illustrated in FIG. 3. The base 7 of the sampling device 3''' illustrated therein contains an optional tool to facilitate the transfer of a collected sample from the base 7 to a separate receptacle, such as a sterile vial (not shown). This tool may be in the form of a spigot or spout 13 from which the collected sample may be poured under controlled conditions. The spigot or spout 13 is present in the base 7 in a fashion so that a collected sample can be safely dispensed from the sampling device 3''' by loosening the lid 5 and pouring the collected sample via spout 13 into a sterile receptacle. Because the sampling device 3''' is leak proof when closed, the lid 5 must be loosened to permit the collected sample to be dispensed via the spout 13. The spigot or spout 13 may be, for example, machined or molded as part of base 7.

Figure 4:
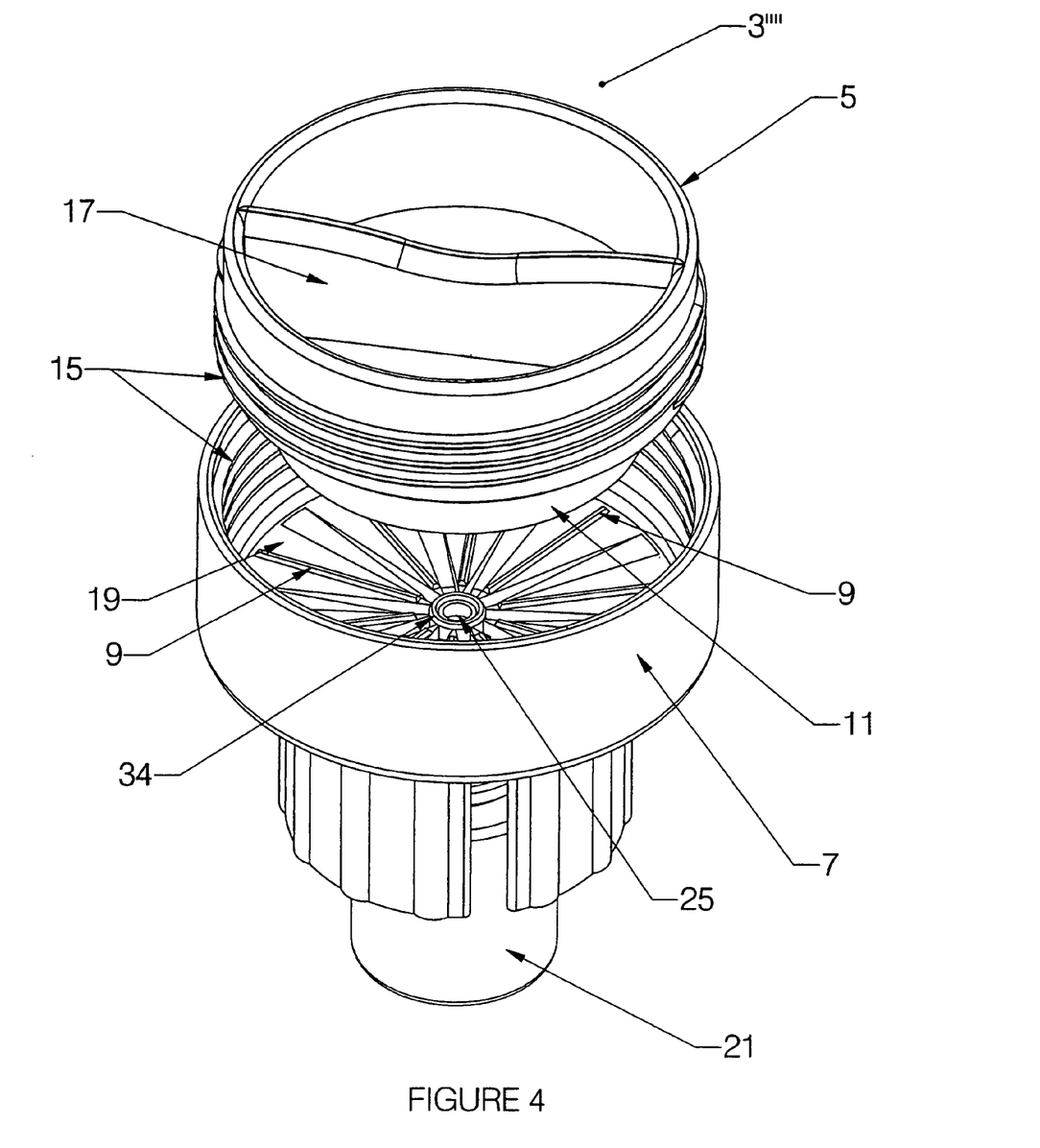

The preferred embodiment of the present invention is set forth in FIG. 4. The sampling device 3'''', therein may be used to collect a sample in the same fashion as the other embodiments described; however, this embodiment further comprises a sterile catch vial 21 within which a collected sample may be directly deposited. In this preferred embodiment, base 7 contains a port 25, under which sterile catch vial 21 is positioned so as to catch collected samples therein. Sterile catch vial 21 is removably attached (i.e., it may be screwed into) to the exterior bottom portion of base 7 beneath port 25. In order to optimize collection of a collected sample into sterile catch vial 21, the interior bottom surface 19 of base 7 may be pitched towards port 25 so that the collected sample flows in that direction and travels therethrough 25 into the catch vial 21. This embodiment is very efficient in that collected samples may be deposited directly into the catch vial 21. There is no need to transfer a sample from the sampling device 3'''' to a separate sterile receptacle. This further reduces the risk of any sample contamination that may occur during transfer of a collected sample to a sterile receptacle. Once a sample is collected in catch vial 21, catch vial 21 may be removed (i.e., unscrewed) from the bottom of the base 7 of the sampling device 3'''' and either capped or an eye-dropper attachment attached thereto to facilitate the testing of collected sample.

Figure 5:
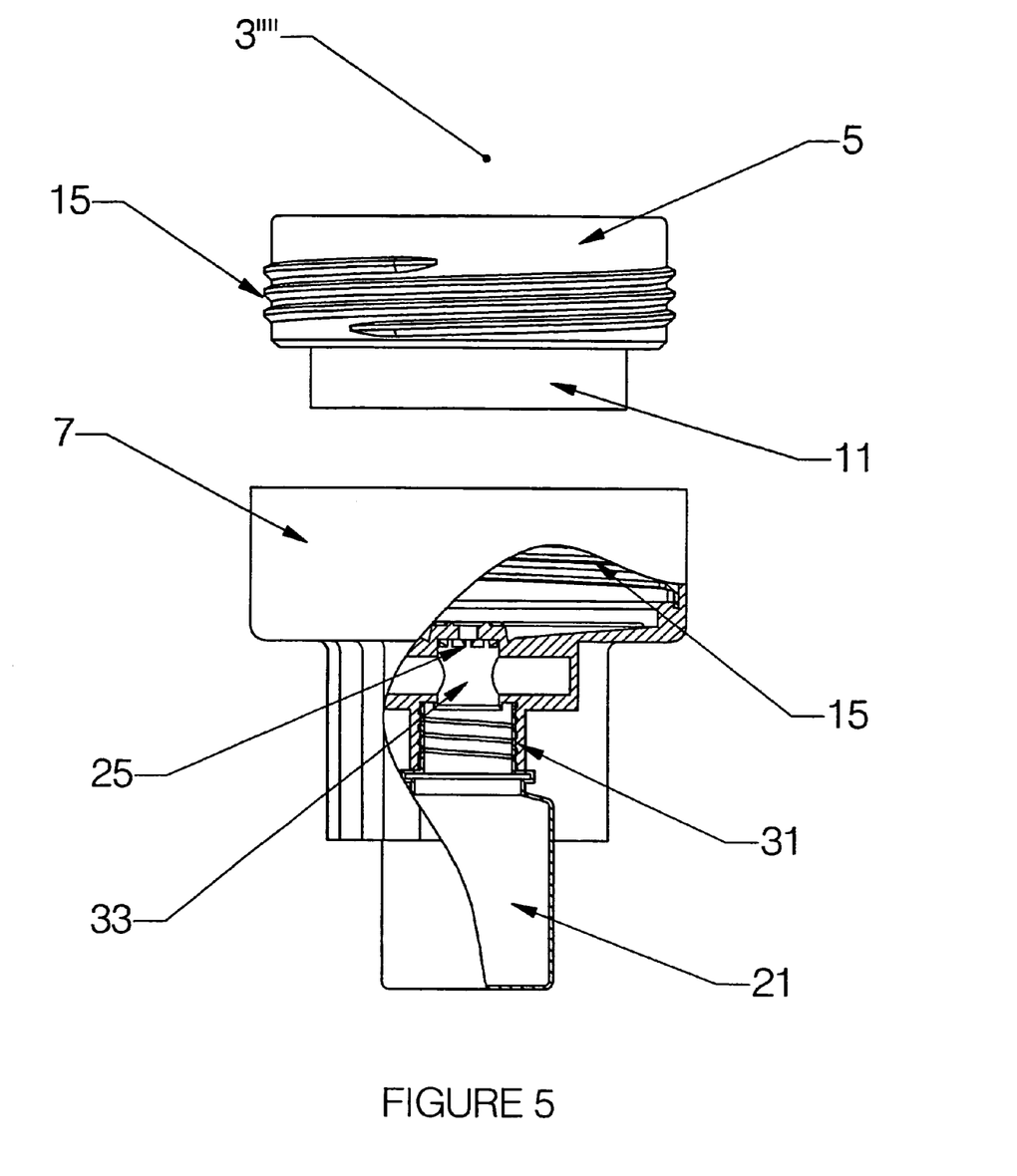

FIG. 5 illustrates a cut-away, schematic view of the preferred embodiment described above and illustrated in FIG. 4. The sterile catch vial 21 is removably attached to the exterior bottom portion of base 7 at adapter means 31. Note that base 7 is configured so that sterile catch vial 21 may be removably positioned beneath port 25 via adapter means 31—i.e., threaded lip, so that collected samples may be deposited directly into said vial 21. After sample collection, the vial 21 containing the sample may be removed (i.e., unscrewed) from the base 7, capped and transported for testing and analysis. As an alternative, the entire sampling device 3'''' with the vial 21 attached thereto and the collected sample therein may be safely transported.

The lid, base, means to facilitate sample recovery (i.e., grooves, ridges, screen, etc.) and any other part of the sampling device within the scope of the present invention, other than the absorbent collection means, that may come into contact with a collected sample may be made from materials that do not react with, off-gas, affect or interfere with the integrity of chemical and biological samples to be collected or the buffer solutions to be employed. Materials which may be employed may be selected from polypropylene, acrylonitrile butadiene styrene (ABS), or any other suitable material that would have the desired properties set forth above. Moreover, these parts of the sampling device may be made using conventional molding and/or machining techniques. One having ordinary skill in the art will be familiar with the types of materials suitable for the purpose described herein as well as the various, suitable methods which may be used for making the sampling device within the scope of the present invention.

It has been determined that various absorbent materials may be suitably employed as the sterile absorbent collection means in the lid of the sampling device. For instance, sponges, pads, foams or other porous, absorbent materials may be employed herein. In determining the type of material suitable for use as the sterile absorbent collection means, consideration is given to its ability to retain water; its ability to release chemical and biological materials following sampling; its strength during vigorous sampling of various surfaces; its compatibility with solvents that may be encountered; and its ease of integration into the lid of the sampling device in a sterile format. Based on these considerations, sponges were determined to be the preferred absorbent collection means. Cellulose-based sponges, polyurethane/polyester blend sponges, Dacron® sponges, and the like may be employed within the scope of the present invention. Based on recovery data, the inventors determined that cellulose-based sponges are preferred. One having ordinary skill in the art would be able to identify materials that are suitable for the prescribed purpose for which the sponges are employed herein.

The sterile absorbent collection means may be integrated into or secured to the interior surface of the lid of the sampling device using any conventional means so long as the means used do not interfere with the integrity of the collection or with the subsequent detection process. For example, insert molding, mechanical fasteners, heat staking, solvent bonding and the like may be employed to accomplish this. Moreover any glue or cement that would not interfere with the integrity of the collection and analysis/detection process may be used as well. One having ordinary skill in the art would be able to select an appropriate means to use that would not contaminate the sampling device or its contents.

The means to facilitate sample recovery (also referred to as sample recovery means) from the sterile absorbent collection means may be, for example, in the form of grooves, ridges, grids, or screens positioned within or molded into the base of the sampling device so as to compress and/or scrape the absorbent collection means when the sampling device is being closed as well as when it is in the closed position. Compression and/or scraping of the absorbent collection means via the sample recovery means forces the collected sample therein to be released therefrom. The released collected sample squirts or drips into the base. Note that the design of the grooves, ridges, grids or screens may vary; and their specific design is not critical to the invention so long as the grooves, ridges, grids or screens serve the purpose for which they are intended. The sample recovery means need not be limited to grooves, ridges, grids or screens; and may be any configuration so long as the purpose for which its presence in the invention is intended is accomplished. One skilled in the art will be able to identify designs and materials suitable for the sample recovery means herein.

During use of the sampling device, a collected sample displaces air present in the sampling device. If the displaced air has no means of escaping, a build up of pressure occurs within the sampling device. To avoid the build up of excess pressure within the sampling device, a means for releasing this pressure without releasing collected sample may be employed. For example, a hole (not illustrated) may be provided in the base of the sampling device—i.e., in the neck 33 of the preferred embodiment (see FIG. 5). The hole may then be covered using a liquid impermeable membrane which allows air to vent from the sampling device. A membrane such as a Duravent™ adhesive vent, manufactured by W. L. Gore Co. (Elkton, Md.) may be employed for this purpose. Duravent™ is a PreVent membrane adhesive patch vent and comprises a GORE-TEX® fiber patch with a permanent adhesive thermoset acrylic pressure sensitive adhesive ring. The fiber comprises expanded PTFE (polytetrafluoroethene) on spunbounded polyester. Use of this membrane prevents the passage of liquid, but allows air to pass freely through the fiber. Therefore, a "closed system" may be maintained. This method of pressure relief allows the reduction of pressure build-up, while simultaneously preventing the loss/leakage of sample liquid. Other means for relieving the pressure build up while preventing the loss of liquid sample are available and may be employed herein. One having ordinary skill in the art, with knowledge of the present invention, would be able to select suitable means to employ for relieving pressure build up.

The present invention also includes a chemical and biological sampling kit that employs the sampling device described above. The kit itself comprises the self-contained sampling device and a vial containing a suitable buffer. The kit may additionally contain a sterile receptacle into which the collected sample may be transferred for analysis. If the kit employs the preferred embodiment herein, which sampling device includes a sterile catch vial, obviously an additional sterile receptacle is not needed. A sterile eye dropper may optionally be included in the sampling kit.

Buffers are used in the present invention to facilitate the sampling and retrieval of chemical and biological materials. For example, the buffer may be added to the sampling device either prior to sample collection or at some point after sample collection. If added to the sample device prior to sample collection, sample collection is performed in the wet state—the sterile absorbent collection device contains buffer therein and the surface from which a sample is sought is sampled using the "wet" absorbent collection device. If not added, obviously sample collection is performed using a dry sterile absorbent collection device—hence, dry state collection is performed. If sample collection is performed in the dry state, the buffer may be added to the absorbent collection device at a later time to facilitate sample retrieval therefrom. As an alternative, the surface from which a sample is sought may be "wet" with a buffer prior to sample collection to facilitate loosening of the sample from the surface so that it can be absorbed using the sampling device of the present invention.

A suitable buffer to use would be one that does not interfere with chemical or biological detection assays employed. Suitable buffers include, but are not limited to, Phosphate Buffered Saline (PBS) and Tris Buffered Saline (TBS). Suitable PBSs have a concentration of approximately 0.005 M to 0.25 M Phosphate Buffer, 0.05 M to 0.2 M sodium chloride (NaCl), and have a pH range of approximately 6.9 to 7.9. The preferred PBS buffer to employ comprises 0.01 M Phosphate Buffer, 0.15 M NaCl and has a pH of 7.4. Suitable TBSs may comprise 0.005 M to 0.3 M Tris, 0.05 M to 0.25 M NaCl and have a pH range of approximately 6.9 to 8.5. The preferred TBS comprises 50 mM Tris, 150 mM NaCl and has a pH of 7.5. NaCl, KCl or other salts may be employed in these buffers, but their presence in these buffers should not exceed 300 mM. As an alternative, water may be substituted for these types of buffers, but it is not preferred because some biological samples are stabilized by utilizing a PBS buffering system. Use of preservatives such as sodium azide, thimerasol, or KATHON in the buffer solutions are avoided as they can inhibit subsequent analysis of the sample. One having ordinary skill in the art of chemical and biological sampling would be able to select a buffer system most suitable to employ in the present invention.

The sampling device of the present invention may be used as follows: The self-contained, sterile sampling device is in the closed position prior to use so as to avoid contamination. This means that the lid is securely positioned on the base—i.e., the lid may be screwed onto the base via threads. Prior to use of the device, a determination is made by an operator as to whether to take a wet or dry sample. If a wet sample is desired, either a sampling device already containing a buffer solution therein is used or the operator opens the sterile sampling device, by removing its lid from the base, and pours a sufficient amount of a buffer solution into the sampling device prior to use. The amount of buffer added is to be sufficient so as to wet the sterile absorbent collection means therein. The lid of the device may be screwed onto the base to seal the fluid and the wetted absorbent collection means until needed. If a dry sample is to be taken, clearly the above does not apply and buffer is not added to the sampling device at this time. The sampling device, wet or dry, is then taken into theatre where a sample is desired. The operator removes the lid from the sampling device; and, while holding the lid having a sterile absorbent collection means attached thereto, swipes the sterile absorbent collection means along the surface from which a sample collection is desired so as to obtain a sample on said absorbent collection means. Once the sample has been collected, the lid is replaced onto the base in fashion so as to prevent any cross contamination between the sample-containing contents of the sampling device and the environment surrounding it. At this point, the sample, which is securely confined in the sampling device, may be safely transported out of theater for retrieval, analysis and archiving.

If the preferred sampling device (see FIGS. 4 and 5) is used for wet sampling, for example, once the sample is collected, replacing the lid on to the base causes the sample to be released from the absorbent collection means and retrieved in the sterile catch vial. The catch vial, containing the collected sample, may be removed from the base, capped and then transported. Note that the sample may be transported in the vial (without/separate from the sampling device). It should be noted, however, that when using the preferred sampling device, the collected sample may also be transported in the sampling device with the catch vial still attached to the base if desired.

If a sample is collected using a dry absorbent collection means, sufficient buffer is added to the sample containing sampling device so as to wet the absorbent collection means and facilitate retrieval of the sample for analysis.

Whether a dry or wet sample was originally collected, they are both retrieved in the wet form. Recovery of the wet sample from the absorbent collection means is accomplished by replacing the lid of the sampling device onto the base. This initiates compression and/or scraping of the sample containing absorbent collection means (i.e., sponge) via the means to facilitate sample recovery (i.e., ridges or grooves), which causes the release of the sample into the base of the sampling device.

Transfer of the collected sample from the base of sampling device 3' or 3" (FIGS. 1 and 2) to a separate sterile receptacle may be accomplished by opening the sampling device and using, for example, a sterile eye dropper or pipette (not shown) or any other sterile, suitable means. In sampling device 3''' (FIG. 3), transfer of the collected sample is accomplished by slightly loosening the lid from the base and carefully pouring the collected sample into a sterile receptacle using the spout. The preferred embodiment of the present invention which is illustrated in FIGS. 4 and 5, provides for a sterile vial that is removably attached to the base. When using this preferred embodiment, the collected sample is deposited directly into the removably attached vial. There is no need to transfer the collected sample to an additional receptacle.

In any of the embodiments within the scope of the present invention, a screw-on eye-dropper attachment may be employed on a sample containing vial/receptacle to provide a means to apply the sample to, for example, a hand held immunoassay or any other testing apparatus. The collected sample may then be analyzed using suitable techniques such as PCR (polymerase chain reaction) or mass spectrometry.

While the chemical and biological sampling device of the present invention is illustrated as being in a cylindrical-type configuration, one having ordinary skill in the art will recognize that the shape of the sampling device need not be so limited. Although the embodiments described employ a lid that screws on to the base, any means for sealing the lid and the base so as to create a leak proof seal for the chemical and biological sampling device may be employed.

While particular embodiments of the present invention have been shown and described, it will be obvious to those skilled in the art that changes and modifications may be made without departing from this invention. Therefore, it is intended that the claims herein are to include all such obvious changes and modifications as fall within the true spirit and scope of this invention.

We claim:

1. A method for collecting a chemical or biological sample, comprising:
   (a) providing a chemical and biological sampling device comprising:
   a base; and
   a lid adapted for sealing to said base in a closed position, wherein said lid includes integrated therein a sterile absorbent collection means for collecting a sample, wherein said sterile absorbent collection means extends a sufficient amount from said lid so as to facilitate sample collection, and wherein said sterile absorbent collection means is positioned in said lid so that when the sampling device is in the closed position said sterile absorbent collection means is on the inside of said sampling device; and
   wherein said base includes therein a means to facilitate sample recovery from said sterile absorbent collection means, and wherein said base further comprises a vent to allow air but not liquid to escape from inside said closed sampling device;
   (b) opening said chemical and biological sampling device by removing said lid from said base;
   (c) sampling a surface from which a sample is desired by swiping said lid with said sterile absorbent collection means therein faced down against said surface so as to collect a sample onto said sterile absorbent collection means; and
   (d) closing said chemical and biological sampling device by returning said lid containing the sample-containing absorbent collection means to said base.

2. The method of claim 1, further comprising adding a buffer to said chemical and biological sampling device prior to the sampling of said surface from which a sample is desired.

3. The method of claim 1, further comprising adding a buffer to said chemical and biological sampling device after the sampling of said surface from which a sample is desired.

4. The method of claim 1, further comprising safely transporting said closed, sample-containing chemical and biological sampling device to a desired location.

5. The method of claim 4, further comprising adding a buffer to said sample containing chemical and biological sampling device once transported to a desired location.

6. The method of claims 2, 3 or 5, further comprising transferring said collected chemical or biological sample along with said buffer from said chemical and biological sampling device to a sterile receptacle.

7. The method of claim 1, wherein said base comprises a tool to facilitate the transfer of a collected sample from said base to a sterile receptacle, further comprising transferring said collected chemical or biological sample to a sterile receptacle using said tool to facilitate the transfer of a collected sample from said base to said sterile receptacle.

8. A method for collecting a chemical or biological sample comprising:
   (a) providing a chemical and biological sampling device comprising:
      a base;
      a lid adapted for sealing to said base in a closed position; and
      a capture vial;
   wherein said lid includes integrated therein a sterile absorbent collection means for collecting a sample, wherein said sterile absorbent collection means extends a sufficient amount from said lid so as to facilitate sample collection, and wherein said sterile absorbent collection means is positioned in said lid so that when the sampling device is in the closed position said sterile absorbent collection means is on the inside of said sampling device; and
   wherein said base includes therein a port and a means to facilitate sample recovery from said sterile absorbent collection means, and wherein said base further comprises a vent to allow air but not liquid to escape from inside said closed sampling device; and
   wherein said capture vial is removably attached to an exterior bottom portion of said base and is positioned beneath said port so as to capture collected samples;
   (b) opening said chemical and biological sampling device by removing said lid from said base;
   (c) sampling a surface from which a sample is desired by swiping said lid with said sterile absorbent collection means therein faced down against said surface so as to collect a sample onto said sterile absorbent collection means; and
   (d) closing said chemical and biological sampling device by returning said lid containing the sample-containing absorbent collection means to said base.

9. The method of claim 8, further comprising adding a buffer to said chemical and biological sampling device prior to the sampling of said surface from which a sample is desired.

10. The method of claim 8, further comprising adding a buffer to said chemical and biological sampling device after the sampling of said surface from which a sample is desired.

11. The method of claim 8, further comprising safely transporting said closed, sample-containing chemical and biological sampling device to a desired location.

12. The method of claim 8, further comprising adding a buffer to said sample containing chemical and biological sampling device once transported to a desired location.

13. The method of claim 9, 10, or 12, further comprising removing and sealing said sample containing capture vial.

* * * * *